US00PP15289P3

(12) United States Plant Patent
Sanders

(10) Patent No.: US PP15,289 P2
(45) Date of Patent: Nov. 2, 2004

(54) ***AGERATUM* PLANT NAMED 'AGSANTIS'**

(50) Latin Name: *Ageratum houstonianum*
Varietal Denomination: Agsantis

(75) Inventor: Monica Sanders, Grootebroek (NL)

(73) Assignee: Syngenta Seeds BV, Enkhuizen (NL)

( * ) Notice: Subject to any disclaimer, the term of this patent is extended or adjusted under 35 U.S.C. 154(b) by 0 days.

(21) Appl. No.: 10/339,805

(22) Filed: Jan. 10, 2003

(65) Prior Publication Data

US 2004/0139511 P1 Jul. 15, 2004

(51) Int. Cl.[7] ..... A01H 5/00

(52) U.S. Cl. ..... Plt./263

(58) Field of Search ..... Plt./263

*Primary Examiner*—Kent Bell

(74) *Attorney, Agent, or Firm*—Edouard G. Lebel; Bruce Vrana

(57) ABSTRACT

A new *Ageratum* plant particularly distinguished by its light purple flower, early flowering, strongly branched plant habit and good growth.

1 Drawing Sheet

Latin name of the genus and species of the plant claimed: *Ageratum houstonianum.*

Varietal denomination: 'Agsantis'.

BACKGROUND OF THE NEW PLANT

The present invention comprises a new distinct cultivar of *Ageratum*, botanically known as *Ageratum houstonianum.* The new cultivar is propagated by cuttings resulting from the cross of 'Q250-1' and 'Q295-1.' 'Q250-1' is a white flowering *Ageratum* having a compact habit. 'Q250-1' is not commercially available and is not known by any synonyms. 'Q295-1' is a white flowering *Ageratum* having a compact habit. 'Q295-1' is not commercially available and is not known by any synonyms.

Neither 'Q250-1' nor 'Q295-1' has not been patented. As a result of this cross the present cultivar was created in 1998 in Enkhuizen, Netherlands and has been repeatably asexually reproduced by cuttings in Enkhuizen, Netherlands, in Gilroy, Calif., United States, in Angers, France and in Sarrians, France over a three-year period. The distinctive characteristics of this new *Ageratum* are stable and reproduced true to type in successive generations of asexual reproduction. It takes 8 to 10 weeks to produce a finished plant, depending on the temperature.

This new *Ageratum* plant is an annual in most climatical zones in the United States, only in zones 9 and 10 it is a perennial plant.

DESCRIPTION OF THE DRAWING

This new *Ageratum* plant is illustrated by the accompanying photographic drawing which shows blooms, buds and foliage of the plant in full color, the color shown being as true as can be reasonably obtained by conventional photographic procedures.

DESCRIPTION OF THE NEW CULTIVAR

The following detailed descriptions set forth the distinctive characteristics of this new *Ageratum* plant. The data which defines these characteristics were collected from asexual reproductions carried out in Enkhuizen, Netherlands. The plant history was taken on 30 weeks old plants, blossomed under natural light and artificial light in a greenhouse. Color readings were taken in a laboratory under ambient light. Color references are primarily to The R.H.S. Colour Chart of The Royal Horticultural Society of London.

TABLE 1

Comparison between the new cultivar 'Agsantis,' its parents and a similar cultivar

| | 'Agsantis' | 'Q250-1' | 'Q295-1' | 'R116' (unpatented) |
|---|---|---|---|---|
| Flower color | Light purple | White | White | Violet |
| Size of capitulum | 4–8 mm | 6–9 mm | 4–8 mm | 7–9 mm |
| Plant height | 15–20 cm | 20–25 cm | 15–20 cm | 20–25 cm |
| Diameter of plant | 35–40 cm | 30–35 cm | 25–30 cm | 15–20 cm |

The plant:

*Classification — botanical.*—*Ageratum houstonianum.*

Parentage:

*Female parent.*—A seedling named 'Q250-1' is one of our seedlings from our Q-generation of plants bred in 1987.

*Pollen parent.*—A seedling named 'Q295-1' is one of our seedlings from our Q-generation of plants bred in 1987.

Plant description:

*Growth habit.*—Ascending, well branched.

*Plant height.*—15–20 cm.

*Spreading area of plant.*—35–40 cm.

*Growth rate.*—Compact.

*Strength.*—Very good.

*Branching character.*—Freely branching and lateral branching at every node.

*Blooming period.*—Year round.

The stem:

*Stem length.*—3–10 cm.

*Diameter.*—1–1.8 mm.

*Shape.*—Round.
*Color.*—RHS 145B.
*Anthocyan pigmentation.*—Absent.
*Length of internode.*—10–20 mm, depending on the light where the plant is propagated.
*Pubescence.*—Slightly pubescent.

The foliage:
*Phyllotaxis.*—Opposite, decussate.
*Shape of blade.*—Ovate.
*Texture.*—Upper side: Slightly pubescent. Lower side: Slightly pubescent.
*Venation.*—Reticulate.
*Leaf margin.*—Serrate.
*Leaf base.*—Cordate.
*Leaf apex.*—Acute.
*Length.*—24–30 mm.
*Width.*—24–30 mm.
*Color.*—Upper side: Dark green 137B. Lower side: Medium green 138B.
*Pubescence.*—Some pubescence is present.
*Length of petiole.*—3–6 mm.
*Diameter of petiole.*—1–2 mm.
*Color of petiole.*—Light green 145B.
*Petiole surface texture.*—Slightly pubescent.

Inflorescence:
*Inflorescence.*—Compound umbel of capitula.
*Number of inflorescence per plant.*—40–70.
*Umbel diameter.*—4–7 cm.
*Umbel debt.*—1.5–3.5 cm.
*Length of peduncle.*—8–15 mm.
*Color of peduncle.*—RHS 138A.
*Diameter of peduncle.*—1–2 mm.
*Length of pedicel.*—4–15 mm.
*Color of pedicel.*—RHS 138A.
*Diameter of pedicel.*—1–2 mm.
*Number of capitula per inflorescence.*—4–7.
*Number of disc florets per capitulum.*—50–80.
*Capitulum in bud stage.*—Round, flat capitulum, showing unopened florets from the start.
*Number of ray florets.*—0.
*Shape of the corolla of the disc floret.*—Actinomorph.
*Number of lobes.*—5.
*Length of disc floret.*—4–5 mm.
*Diameter of disc floret.*—1–2 mm.
*Color of disc floret upper side.*—RHS N87 B.
*Color of disk floret lower side.*—RHS 155 C.
*Number of phyllaries per capitulum.*—15–20.
*Length of phyllaries.*—4–5 mm.
*Diameter of phyllaries.*—1–2 mm.
*Color of phyllaries.*—Upper side: RHS 138 A. Lower side: RHS 138 A.
*Diameter of capitulum at beginning of flowering.*—2–5 mm.
*Depth of capitulum.*—3–4 mm.
*Color of capitulum at beginning of flowering.*—RHS N87B.
*Diameter of capitulum at full flowering.*—4–8 mm.
*Color of capitulum at full flowering.*—RHS N87B.

Reproductive organs:
Gynoecium:
*Number of pistils.*—1.
*Shape of pistils.*—Style with two filiform branches.
*Length of stigma and style.*—4–6 mm.
*Color of stigma.*—RHS N88C.
*Inferior ovary.*—5 ribbed.
*Pappus.*—Short.

Androecium:
*Number of anthers.*—5, connate in a tube, filaments free.
*Shape of anthers.*—Ecalcarate.
*Pollen.*—Pollen is abundantly present.
*Color of pollen.*—RHS N155 A.
*Fragrance.*—No fragrance.
*Lastingness of the bloom.*—The capitula of one umbel open over a period of 3–4 weeks. It takes 3–4 weeks until all disc florets of one umbel are opened.
*Seedset.*—'Agsantis' has seedset.

Seed:
*Shape.*—Pentagonal.
*Length.*—2 mm.
*Diameter.*—0.8 mm.
*Color.*—RHS 202A.
*Pappus.*—Very short.

Roots:
*Type of roots.*—Fibrous. Roots start to grow on every part of the stem that contacts the soil, so not only at the nodes.

Physiological and ecological characteristics: Good tolerance to heat and cold, but no frost tolerance. Strong resistance to pests and diseases.

What is claimed is:

1. A new and distinct variety of *Ageratum* plant, substantially as illustrated and described herein.

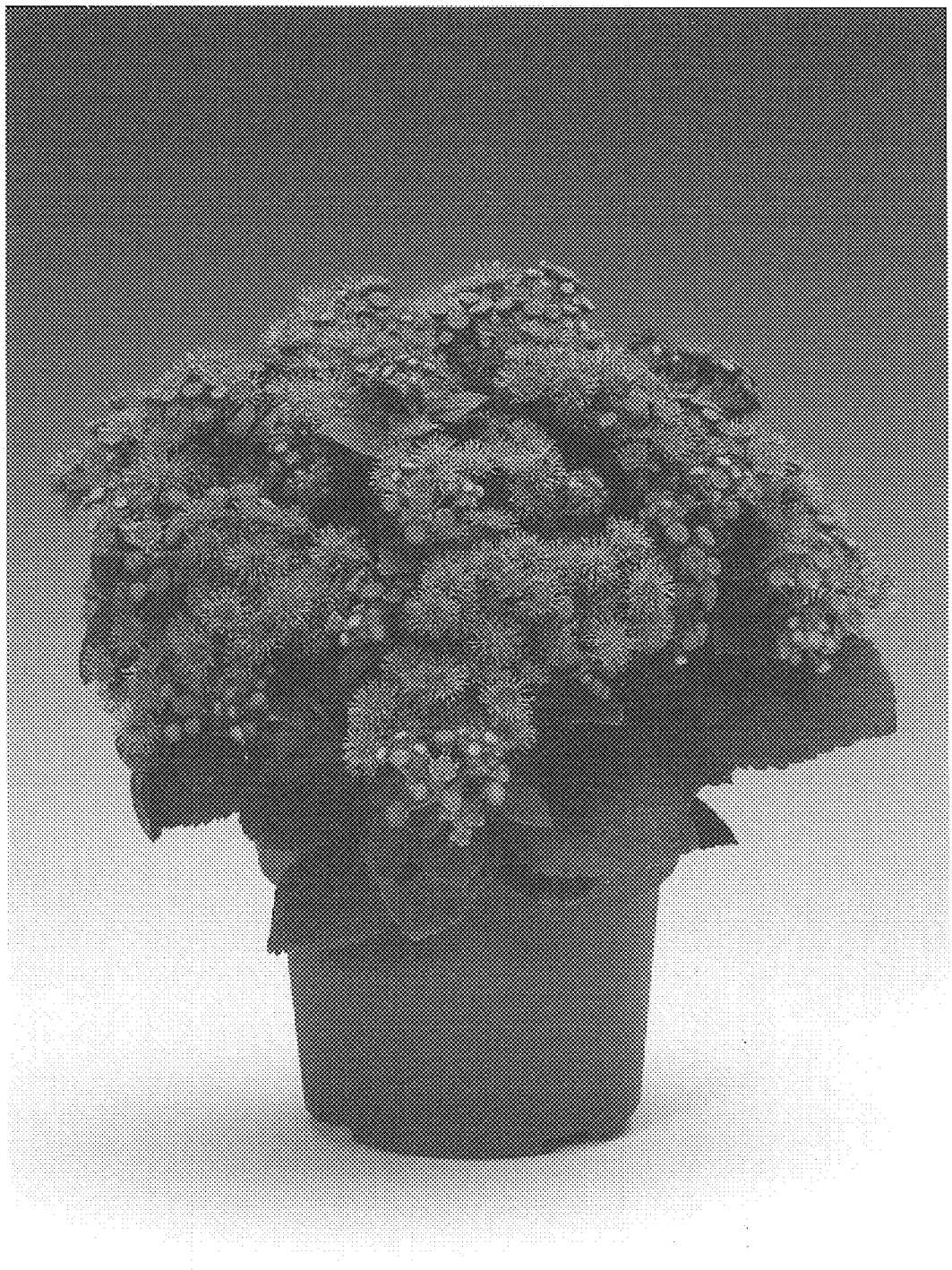

* * * * *